United States Patent [19]

Sarantakis

[11] 4,440,904
[45] Apr. 3, 1984

[54] NONAPEPTIDE ANTI-SECRETORY AGENTS

[75] Inventor: Dimitrios Sarantakis, West Chester, Pa.

[73] Assignee: American Home Products Corporation, New York, N.Y.

[21] Appl. No.: 462,168

[22] Filed: Jan. 31, 1983

[51] Int. Cl.³ .................... C08L 89/00; C07C 103/52; A61K 37/00
[52] U.S. Cl. .......................... 525/54.11; 260/112.5 S; 424/177
[58] Field of Search .............. 260/112.5 S; 525/54.11; 424/177

[56] References Cited

U.S. PATENT DOCUMENTS 4,282,143 8/1981 Sarantakis ........................ 260/112.5

OTHER PUBLICATIONS

Veber et al., Nature 280, 512–514 (1979).
Brazeau et al., Science 179, 77–79 (1973).

*Primary Examiner*—Delbert R. Phillips

*Attorney, Agent, or Firm*—Richard K. Jackson

[57] ABSTRACT

The nonapeptides

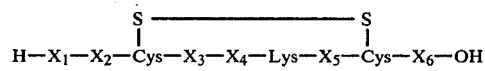

in which $X_1$ is either L- or D- His, Lys or Arg;
$X_2$ is either L- or D- Phe, Tyr, Trp, Leu, Met, His, Glu or Asp;
$X_3$ is Phe, Tyr, Trp, Leu or Met;
$X_4$ is L- or D-Trp;
$X_5$ is Thr, Val or Abu; and,
$X_6$ is either L- or D- Phe, Tyr, Trp, Leu, Met, Ser or Thr;

the linear precursor intermediates and pharmaceutically acceptable salts and amides thereof are inhibitors of growth hormone release and are anti-secretory agents which act as $H_2$-receptor antagonists.

4 Claims, No Drawings

NONAPEPTIDE ANTI-SECRETORY AGENTS

SUMMARY OF THE INVENTION

Nonapeptides of the formula:

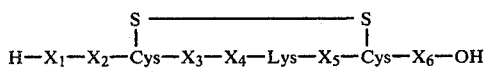

in which $X_1$ is either L- or D-His, Lys or Arg;

$X_2$ is either L- or D-Phe, Tyr, Trp, Leu, Met, His, Glu or Asp;

$X_3$ is Phe, Tyr, Trp, Leu or Met;

$X_4$ is L- or D-Trp;

$X_5$ is Thr, Val or Abu; and, $X_6$ is either L- or D-Phe, Tyr, Trp, Leu, Met, Ser or Thr;

the linear precursor intermediates thereof, pharmaceutically acceptable salts and amides thereof, are inhibitors of growth hormone release. In addition, the polypeptides of this invention are anti-secretory agents in that they reduce (1) total gastric volume, (2) hydrogen ion secretion, or (3) hydrogen ion concentration.

The reduction of any one of these parameters aids in attenuating the general debilitating influence of a peptic ulcer. The use of compounds exhibiting anti-secretory activity in the curative and/or prophylactic treatment of peptic ulcer disease is an established, beneficial procedure.

DETAILED DESCRIPTION OF THE INVENTION

In accordance with this invention there is provided a group of nonapeptides of the formula:

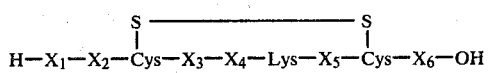

in which $X_1$ is either L- or D-His, Lys or Arg;

$X_2$ is either L- or D-Phe, Tyr, Trp, Leu, Met, His, Glu or Asp;

$X_3$ is Phe, Tyr, Trp, Leu or Met;

$X_4$ is L- or D-Trp;

$X_5$ is Thr, Val or Abu; and, $X_6$ is either L- or D-Phe, Tyr, Trp, Leu, Met, Ser or Thr;

the linear precursor intermediates thereof and pharmaceutically acceptable salts and amides thereof. In the definitions of $X_1$, $X_2$ and $X_6$ it is intended that the expression "either L- or D-" modify each of the members of the defined series.

The pharmaceutically acceptable salts of the compounds of this invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic or ascorbic acid and the like. Similarly the C-terminal carboxylic acid salts of alkali metals and ammonia are produced by careful neutralization of the acid. By amides of the compounds disclosed herein, applicant intends to embrace alkyl amides containing from 1 to 4 carbon atoms, which amides are produced conventionally.

The linear precursor intermediates of the cyclic nonapeptides of this invention may be depicted as follows:

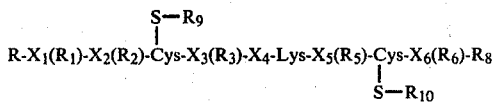

where $X_1$–$X_6$ are defined above, and

R is hydrogen or an alpha amino protecting group;

$R_1$ is hydrogen or an amino protecting group;

$R_2$ is hydrogen, a phenolic hydroxy protecting group for tyrosine, an amino protecting group for histidine or a carboxy protecting group for glutamic or aspartic acid;

$R_3$ is hydrogen or a phenolic hydroxy protecting group;

$R_5$ is hydrogen or a hydroxyl protecting group;

$R_6$ is hydrogen or a hydroxyl protecting group;

$R_8$ is —$NHR_{10}$, in which $R_{10}$ is alkyl of 2 to 4 carbon atoms, or —$OR_{11}$, in which $R_{11}$ is hydrogen or alkyl of 1 to 6 carbon atoms or —$OCH_2$ (resin support);

$R_9$ and $R_{10}$ are hydrogen or sulfhydryl protecting groups.

These intermediates comprise the fully protected and partially protected nonapeptides bound to a resin support employed in solid phase synthesis of the polypeptide as well as the fully deprotected linear polypeptide removed from the resin support.

The protecting groups employed during preparation of the linear intermediates are conventional in solid phase polypeptide synthesis. Thus, in the above formula, the protecting group embraced in the definition of R may be formyl, trifluoroacetyl, phthalyl, p-chlorobenzyloxycarbonyl, p-nitrobenzyloxycarbonyl, tert-butyloxycarbonyl (BOC), 2,2,2-trichloroethoxycarbonyl, amyloxycarbonyl, cyclopentyloxycarbonyl, cyclohexyloxycarbonyl, trityl, etc., the preferred group being tert-butyloxycarbonyl.

Examples of the sulfhydryl protecting groups $R_9$ and $R_{10}$ and the hydroxyl protecting groups $R_{2-6}$ of tyrosyl, seryl or threonyl are benzyl, p-methoxybenzyl, p-chlorobenzyl, p-nitrobenzyl, p-methyl-benzyl, trityl, benzyloxycarbonyl, p-methoxybenzyloxycarbonyl and the like. The p-methylbenzyl group is preferred for protection of cysteinyl sulfur while the benzyl group is preferred for seryl and threonyl and 2,6-dichlorobenzyl is preferred for tyrosyl.

Protecting groups for the nitrogen atom of lysine include tosyl, benzyloxycarbonyl, 2-chlorobenzyloxycarbonyl, and tert-butyloxycarbonyl, preferably the 2-chloro-benzyloxycarbonyl group.

Protecting groups for arginine and histidine include nitro, tosyl, benzyloxycarbonyl, adamantyloxycarbonyl and tert-butyloxycarbonyl. Where the protecting group is nitro or tosyl, the protection is on either one of the $N^\omega$, $N^{\omega'}$ nitrogens and in the case of benzyloxycarbonyl, or adamantyloxycarbonyl, the protection is on the $N^\delta$ nitrogen and either one of the $N^\omega$, $N^{\omega'}$ nitrogen atoms of arginine. The preferred protecting group is benzyloxycarbonyl.

Protecting groups for the carboxyl groups of glutamic acid and aspartic acid are ester or anhydride derivatives which are not removed during removal of the α-amino protecting group. Preferably the benzylester is employed to protect the carboxyl group.

The criterion for selecting protecting groups for R-R$_9$ are (a) the protecting group must be stable to the reagent and under the reaction conditions selected for removing the α-amino protecting group at each step of the synthesis, (b) the protecting group must retain its protecting properties (i.e. not be split off under coupling conditions), and (c) the protecting group must be readily removable upon conclusion of the polypeptide synthesis, under conditions that do not otherwise effect the polypeptide structure.

The nonapeptides of this invention may be prepared by either solid phase or liquid phase methodology, well known to the art. The support employed in the solid phase synthesis of the compounds of this invention is a chloromethylated or hydroxymethylated polystyrene resin cross-linked with divinylbenzene. Such resin supports are prepared by known methods and are commercially available.

The following examples illustrate the preparation of H-His-Tyr-Cys-Phe-D-Trp-Lys-Thr-Cys-Phe (3,8-disulfide) which is representative in its solid phase preparation and biological activity, of the other compounds of the invention generically described, supra.

EXAMPLE 1

N$^\alpha$-tert-Butyloxycarbonyl-N$^{im}$-benzyloxycarbonyl-L-histidyl-O-2,6-dichloro-benzyl-L-tyrosyl-S-4-methylbenzyl-L-cysteinyl-L-phenylalanyl-D-tryptophyl-N$^\epsilon$-2-chlorobenzyloxycarbonyl-L-lysyl-O-benzyl-L-threonyl-S-4-methylbenzyl-L-cysteinyl-L-phenylalanine hydroxymethyl polystyrene ester

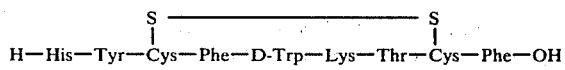

Chloromethylated polystyrene resin (Lab. Systems Inc.) 1% cross linked with divinylbenzene was esterified with BOC-L-Phe-OH cesium salt according to Gisin, *Helv. Chim. Acta,* 56, 1976 (1973). The polystyrene resin ester was placed in a solid phase peptide synthesis reaction vessel and treated according to Schedule A for the incorporation of BOC-Cys(SMB)OH, BOC-Thr(BZL)OH, BOC-Lys-(ClZ)OH, BOC-D-Trp-OH, BOC-Phe-OH, BOC-Cys(SMB)OH, BOC-Tyr(Cl$_2$-BZL)OH and finally BOC-His(CBZ)OH to afford the title peptidoresin (14.6 g).

Schedule A

1. Wash with methylene chloride (CH$_2$Cl$_2$), three times.
2. Treat with trifluoroacetic acid-methylene chloride (1:1, v/v) containing 5% 1,2-ethane dithiol for 5 minutes.
3. Repeat Step 2 for 25 minutes.
4. Wash with CH$_2$Cl$_2$;, three times.
5. Wash with dimethylformamide (DMF).
6. Treat with 12% triethylamine in DMF for 3 minutes.
7. Wash with DMF.
8. Wash with CH$_2$Cl$_2$, three times.
9. Treat with 4 equivalents of the appropriate protected amino acid in CH$_2$Cl$_2$-DMF and stir for 5 minutes.
10. Add in two portions over a 30 minute period, 5 equivalents of diisopropylcarbodiimide dissolved in CH$_2$Cl$_2$. Allow reaction to proceed for 6 hours.
11. Wash with DMF, three times.
12. Wash with CH$_2$Cl$_2$, three times.
13. Test by ninhydrin reaction according to the procedure of Kaiser et al., *Annal. Biochem.,* 34, 595 (1970). In case of incomplete reaction, repeat Steps 9 to 13, as above.

EXAMPLE 2

L-Histidyl-L-tyrosyl-L-cysteinyl-L-phenylalanyl-D-tryptophyl-L-lysyl-L-threonyl-L-cysteinyl-L-phenylalanine cyclic (3–8) disulfide

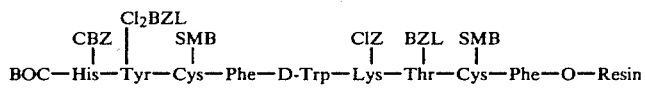

The peptidoresin of the previous example (14.6 g) was mixed with anisole (20 ml) and treated with liquid, anhydrous HF (200 ml) for 60 minutes in an ice bath after which time the excess HF was removed under vacuo as fast as possible and the residue was taken in 100 ml of 50% aqueous AcOH. The mixture was filtered and the filtrate was poured into 6 liters of deaerated water. The pH was brought to 6.8 with dilute NH$_4$OH and then the mixture was oxidized with a solution of K$_3$Fe(CN)$_6$ (3 g in 500 ml H$_2$O). The yellow solution was brought to pH 5 with gl. AcOH and then it was treated with Bio Rad AG3-X4A (Cl-form) for 30 minutes, filtered and the filtrate was passed through Bio Rex 70 (H+ form) to absorb the peptidic material. The cation exchange resin was eluted with a mixture of H$_2$O-Pyridine-AcOH (66:30:4) and the fractions containing the peptide were lyophilized to afford a solid, 1.24 g. The crude material was chromatographed through a column of Sephadex G25 (2.5×150 cm) and eluted with 10% aq-AcOH. Fractions (120 drops each) 117–128 were pooled and lyophilized to yield 480 mg of the title compound as the acetate salt.

TLC Silica gel 60 precoated glass plates.

R$_f$ (EtOAc-n-BuOH-H$_2$O-AcOH, 1:1:1:1, v/v) 0.60 trace at 0.65.

R$_f$ (EtOAc-n-BuOH-H$_2$O-Pyridine-AcOH, 1:1:1:0.6:0.6, v/v) 0.75 trace at 0.79.

HPLC Reverse phase Vydac C$_{18}$ column, elution with CH$_3$CN 25%-1M-NH$_4$H$_2$PO$_4$, pH 3.5 buffer 75%, 2 ml/min, major peak 85.4%.

Aminoacid Analysis: Phe(2) 2; Cys(2) 1.67; Thr(1) 0.97; Tyr(1) 0.98; Lys(1) 1.02; His(1) 0.98; Trp(1) 0.93

The product of the preceding example illustrates the activity of the compounds of this invention for growth hormone suppression in the following standard procedure:

Albino male rats are administered Nembutal intraperitoneally at a dose of 50 milligrams per kilogram. Fifteen minutes later a subcutaneous injection of the compound of Example 2 or physiological saline (control) is administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot is assayed for growth hormone (GH) by radioimmunoassay. The results of the assay are as follows:

| Compound | Dose μg/kg | Time minutes | GH ng/ml |
|---|---|---|---|
| Saline | — | 15 | 90 ± 14 |
| Example 2 | 200 | 15 | 31 ± 10* |
| Example 2 | 1,000 | 15 | 41 ± 8* |
| Somatostatin | 200 | 15 | 34 ± 3* |

*p <0.01

Thus, the compound of Example 2 is substantially equipotent with somatostatin in growth hormone suppression.

In addition, the product of Example 2, which is representative of the other compounds of this invention, was shown to be an effective anti-secretory agent by virtue of its activity in the following scientifically recognized standard test for gastric anti-secretory activity:

Male Charles River rats of Sprague-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered subcutaneously. The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1 N NaOH. The calculated product of gastric volume (ml/4 hr) and acid concentration (mEq/L) estimates the total acid output (TAO, mEq/4 hr) over the four-hour test period. An analysis of variance is performed on these data to determine statistically significant ($p<0.05$) deviation between control versus drug-treated groups.

The product of Example 2 decreased total acid output by 73 percent at a 2 milligram per kilogram dose.

From this it is clear that the compounds of this invention are useful in the treatment of peptic ulcer disease, especially in the patient suffering from acromegaly, where combined reductions in growth hormone and gastric acid output is desireable. Where the conditions of excessive growth hormone secretion and gastric acid output occur separately, the second activity of the compounds of this invention is either inconsequential or of no deleterious effect that would be contraindicative of applicability of use in treatment, as a decrease in growth hormone secretion does not interfere with treatment of peptic ulcer disease.

For either use, the dosage regimen will vary with the mode of administration, size and age of the subject treated as well as the severity of the dysfunction. Thus, administration of the compounds of this invention must be under the guidance and instruction of a physician.

The compounds of this invention may be administered by conventional oral or parenteral routes as solids, liquids or nebulized suspensions. Conventional adjuvants known to the art may be combined with the antisecretory agents of this invention to provide compositions and solutions for administrative purposes, although it is considered desirable and feasible to use neat or pure compounds without additives other than for the purpose of providing suitable pharmaceutically acceptable solution or liquid or vapor suspensions.

What is claimed is:

1. A compound of the formula:

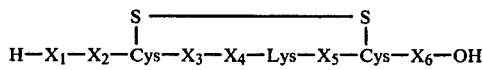

in which
$X_1$ is either L- or D-His, Lys or Arg;
$X_2$ is either L- or D-Phe, Tyr, Trp, Leu, Met, His, Glu or Asp;
$X_3$ is Phe, Tyr, Trp, Leu or Met;
$X_4$ is L- or D-Trp;
$X_5$ is Thr, Val or Abu; and,
$X_6$ is either L- or D-Phe, Tyr, Trp, Leu, Met, Ser or Thr;
the linear precursor intermediates thereof, pharmaceutically acceptable salts and amides thereof.

2. The compound of claim 1 which is L-Histidyl-L-tyrosyl-L-cysteinyl-L-phenylalanyl-D-tryptophyl-L-lysyl-L-threonyl-L-cysteinyl-L-phenylalanine cyclic (3–8) disulfide.

3. A compound of claim 1 of the formula:

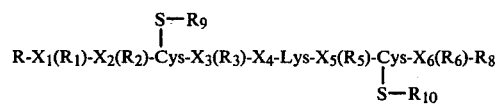

in which
$X_1$ is either L- or D-His, Lys or Arg;
$X_2$ is either L- or D-Phe, Tyr, Trp, Leu, Met, His, Glu or Asp;
$X_3$ is Phe, Tyr, Trp, Leu or Met;
$X_4$ is L- or D-Trp;
$X_5$ is Thr, Val or Abu;
$X_6$ is either L- or D-Phe, Tyr, Trp, Leu, Met, Ser or Thr; and,
R is hydrogen or an alpha amino protecting group;
$R_1$ is hydrogen or an amino protecting group;
$R_2$ is hydrogen, a phenolic hydroxy protecting group for tyrosine, an amino protecting group for histidine or a carboxy protecting group for glutamic or aspartic acid;
$R_3$ is hydrogen or a phenolic hydroxy protecting group;
$R_5$ is hydrogen or a hydroxyl protecting group;
$R_6$ is hydrogen or a hydroxyl protecting group;
$R_8$ is —$NHR_{10}$, in which $R_{10}$ is alkyl of 2 to 4 carbon atoms, or —$OR_{11}$, in which $R_{11}$ is hydrogen or alkyl of 1 to 6 carbon atoms or —$OCH_2$ (resin support);
$R_9$ and $R_{10}$ are hydrogen or sulfhydryl protecting groups.

4. The compound which is $N^\alpha$-tert-Butyloxycarbonyl-$N^{im}$-benzyloxycarbonyl-L-histidyl-O-2,6-dichlorobenzyl-L-tyrosyl-S-4-methylbenzyl-L-cysteinyl-L-phenylalanyl-D-tryptophyl-$N^\epsilon$-2-chlorobenzyloxycarbonyl-L-lysyl-O-benzyl-L-threonyl-S-4-methylbenzyl-L-cysteinyl-L-phenylalanine hydroxymethyl polystyrene ester.

* * * * *